US008460718B2

(12) United States Patent
Zelkha et al.

(10) Patent No.: US 8,460,718 B2
(45) Date of Patent: Jun. 11, 2013

(54) SYNERGISTIC COMPOSITIONS AND METHODS

(75) Inventors: Morris Zelkha, Ramat Gan (IL); Yoav Blatt, Rehovot (IL); Yossi Levy, Omer (IL); Yoav Sharoni, Omer (IL)

(73) Assignee: LycoRed Ltd. (IL)

( * ) Notice: Subject to any disclaimer, the term of this patent is extended or adjusted under 35 U.S.C. 154(b) by 105 days.

(21) Appl. No.: 13/081,643

(22) Filed: Apr. 7, 2011

(65) Prior Publication Data

US 2012/0258182 A1 Oct. 11, 2012

(51) Int. Cl.
*A01N 65/00* (2009.01)

(52) U.S. Cl.
USPC ........................................................ 424/725

(58) Field of Classification Search
None
See application file for complete search history.

(56) References Cited

U.S. PATENT DOCUMENTS

| | | | |
|---|---|---|---|
| 5,837,311 | A | 11/1998 | Zelkha et al. |
| 7,641,931 | B2 | 1/2010 | Zelkha et al. |
| 2005/0031557 | A1 | 2/2005 | Gaertner et al. |
| 2005/0214383 | A1 | 9/2005 | Bubnis et al. |
| 2006/0116334 | A1 | 6/2006 | Hendrix |
| 2007/0298097 | A1 | 12/2007 | Kuo |
| 2008/0260771 | A1 | 10/2008 | Olalde Rangel |
| 2009/0239825 | A1 | 9/2009 | Kuo |
| 2009/0297683 | A1 | 12/2009 | Zelkha et al. |
| 2009/0312287 | A1 | 12/2009 | Kuo |
| 2010/0196563 | A1 | 8/2010 | Zelkha et al. |
| 2010/0239553 | A1 | 9/2010 | Bartunek et al. |

FOREIGN PATENT DOCUMENTS

| | | |
|---|---|---|
| EP | 1997487 A1 | 12/2008 |
| JP | 2007197328 A | 8/2007 |
| WO | 0126668 A1 | 4/2001 |
| WO | 2006041930 A2 | 4/2006 |
| WO | 2012049534 A1 | 4/2012 |

OTHER PUBLICATIONS

International Search Report and Written Opinion for Application No. PCT/IL2012/050128 dated Jul. 10, 2012.
Chen et al., "Phytochemical composition of nuts", Asia Pac J Clin Nutr 2008:17 (SI): 329-332.
Tomatoes, tomato-rich foods, lycopene and cancer of the upper aerodigestive tract: a case-control in Uruguary, De Stefani, et al., Pergamon, Oral Oncology 36 (2000) pp. 47-53.
Tomato Extract Containing Lycopene, Lycopene/Dietary Supplements, USP 28, May 27, 2005, pp. 2-3.
Weststrate, J. A. and Meijer, G. W. Plant sterol-enriched margarines and reduction of plasma total- and LDL-cholesterol concentrations in normocholesterolaemic and mildly hypercholesterolaemic subjects, Eur J Clin Nutr. 52: 334-43, 1998.
Jones, P. J. and Raeini-Sarjaz, M. Plant sterols and their derivatives: the current spread of results, Nutr Rev. 59: 21-4, 2001.
Ling, W. H. and Jones, P. J. Dietary phytosterols: a review of metabolism, benefits and side effects, Life Sci. 57: 195-206, 1995.
Moghadasian, M. H. Pharmacological properties of plant sterols in vivo and in vitro observations, Life Sci. 67: 605-15, 2000.
Awad, A. B., Garcia, M. D., and Fink, C. S. Effect of dietary phytosterols on rat tissue lipids, Nutr Cancer. 29: 212-6, 1997.
Moreno, J. J. Effect of olive oil minor components on oxidative stress and arachidonic acid mobilization and metabolism by macrophages RAW 264.7, Free Radic Biol Med. 35: 1073-81, 2003.
Hui-lian, W., Qian-rong, L., jian, Y., Zhao-feng, L., and Yu-zhen, W. The protective effect and mechanism of soybean oil and its extracts on DNA damage in human ECV304 cells exposed to UV-C, Biochim Biophys Acta. 1626: 19-24, 2003.
Choi, Y. H., Kong, K. R., Kim, Y. A., Jung, K. O., Kil, J. H., Rhee, S. H., and Park, K. Y. Induction of Bax and activation of caspases during beta-sitosterol-mediated apoptosis in human colon cancer cells, Int J Oncol. 23: 1657-62, 2003.
Bouic, P. J. The role of phytosterols and phytosterolins in immune modulation: a review of the past 10 years, Curr Opin Clin Nutr Metab Care. 4: 471-5, 2001.
Awad, A. B., Chen, Y. C, Fink, C. S., and Hennessey, T. beta-Sitosterol inhibits HT-29 human colon cancer cell growth and alters membrane lipids, Anticancer Res. 16: 2797-804, 1996.
von Holtz, R. L., Fink, C. S., and Awad, A. B. beta-Sitosterol activates the sphingomyelin cycle and induces apoptosis in LNCaP human prostate cancer cells, Nutr Cancer. 32: 8-12, 1998.
Awad, A. B., Downie, A. C., and Fink, C. S. Inhibition of growth and stimulation of apoptosis by beta-sitosterol treatment of MDA-MB-231 human breast cancer cells in culture, Int J Mol Med. 5: 541-5, 2000.
Ju, Y. H., Clausen, L. M., Allred, K. F., Almada, A. L., and Helferich, W. G. beta-Sitosterol, beta-Sitosterol Glucoside, and a Mixture of beta-Sitosterol and beta-Sitosterol Glucoside Modulate the Growth of Estrogen-Responsive Breast Cancer Cells In Vitro and in Ovariectomized Athymic Mice, J Nutr. 134: 1145-51, 2004.
Awad, A. B. , Burr, A. T., and Fink, C. S. Effect of resveratrol and beta-sitosterol in combination on reactive oxygen species and prostaglandin release by PC-3 cells, Prostaglandins Leukot Essent Fatty Acids. 72: 219-26, 2005.
Normen, L., Shaw, C. A., Fink, C. S., and Awad, A. B. Combination of phytosterols and omega-3 fatty acids: a potential strategy to promote cardiovascular health, Curr Med Chem Cardiovasc Hematol Agents, 2: 1-12, 2004.
de Jong, A., Plat, J., and Mensink, R. P. Metabolic effects of plant sterols and stanols (Review), J Nutr Biochem. 14: 362-9, 2003.
Judd, J. T., Baer, D. J., Chen, S. C., Clevidence, B. A., Muesing, R. A., Kramer, M., and Meijer, G. W. Plant sterol esters lower plasma lipids and most carotenoids in mildly hypercholesterolemic adults, Lipids. 37: 33-42, 2002.
Richelle, M., Enslen, M., Hager, C., et al. Both free and esterified plant sterols reduce cholesterol absorption and the bioavailability of beta-carotene and alpha-tocopherol in normocholesterolemic humans, Am J Clin Nutr. 80: 171-7, 2004.
Valsta et al., British Journal of Nutrition (2004), 92, 671?678.

*Primary Examiner* — Michael Meller
(74) *Attorney, Agent, or Firm* — Lerner, David, Littenberg, Krumholz & Mentlik, LLP (57) ABSTRACT

Pharmaceutical compositions for oral administration comprising a therapeutically effective amount of a synergistic combination of lycopene and at least one phytosterol wherein the ratio of said lycopene to said phytosterol in said pharmaceutical composition is a maximum of about 5:1 and wherein said composition produces a synergistic inhibition of cell growth are disclosed.

5 Claims, 3 Drawing Sheets

FIG. 1A
β-SITOSTEROL

FIG. 1B
β-CAMPESTEROL

FIG. 1C
OCTASTEROL

FIG. 1D
STIGMASTEROL

FIG. 1E
E. LYCOPENE

SYNERGISTIC COMPOSITIONS AND METHODS

FIELD OF THE INVENTION

The present invention relates to specific carotenoids which are primarily found in tomatoes. More particularly, the present invention relates to combinations of specific carotenoids and phytosterols commonly found in various food products, including tomatoes. Still more particularly, the present invention relates to combinations of these compounds used in pharmaceutical compositions and exhibiting synergistic properties, particularly in the inhibition of prostate cell growth.

BACKGROUND OF THE INVENTION

Carotenoids are a group of pigments that are characterized by color including and ranging from yellow to red. Carotenoids are commonly produced by a wide variety of plant materials and most commonly associated with plants such as tomatoes, carrots and peppers.

Lycopene and its precursors, phytoene and phytofluene, are commonly found in tomatoes and lycopene is the predominant source of the bright red color associated with tomatoes. Phytoene is a precursor of phytofluene, lycopene and other carotenoids, and is also found in high concentrations in tomatoes. Lycopene is generally present in the plasma of the human body. Carotenoids are known to have antioxidant properties and consequently, provide numerous beneficial health effects including reduction of the potential risks of cardiovascular diseases, and cancers, as well as slowing and/or reversing the degenerative effects of aging on various human physiological activities.

Phytosterols (plant sterols) are a group of steroid alcohols, or phytochemicals which are naturally occurring in plants, and are the counterparts of cholesterol in animal products. The structure is similar to that of cholesterol with some modifications. These modifications involve a side chain and include the addition of a double bond and/or methyl or ethyl group. The most common dietary phytosterols are β-sitosterol, Campesterol and Stigmasterol. The Western diet contains 80 mg β-sitosterol/day. In the Finnish diet, 140-175 mg/day (see Valsta et al., British Journal of Nutrition (2004), 92, 671-678), whereas vegetarian and Japanese diets contain 345 and 400 mg/day, respectively. The best dietary sources of phytosterols are unrefined plant oils, seeds, nuts and legumes. Processing of plant oils (such as refining and deodorization) reduces phytosterol content, but the loss varies with the type of oil. However, hydrogenation of refined oils has little effect on phytosterol content.

Plant sterols and stanols effectively reduce serum LDL cholesterol and atherosclerotic risk (1). In addition, potential effects of plant sterols and stanols on other metabolic processes remain to be elucidated (2).

Phytosterols are not endogenously synthesized in the body, and therefore they are derived solely from the diet by means of intestinal absorption. The plasma phytosterol level in mammalian tissue is usually very low, primarily due to poor absorption from the intestine and faster excretion from the liver as compared to cholesterol (3). Although absorption of plant sterols and stanols (0.02-3.5%) is low compared to cholesterol (35-70%), small amounts are found in the blood and may influence certain physiological functions. Intestinal phytosterol absorption is selective; in animals Campesterol is better absorbed than β-sitosterol, while Stigmasterol is only absorbed minimally. Only 0.3-1.7 mg/dl of phytosterols are found in human serum under normal conditions, in spite of daily dietary intakes of 160-360 mg/day. Total plasma plant sterol concentrations in healthy adults range from 7 μmol/L to 24 μmol/L, which accounts for less than 1% of total plasma sterol concentrations (4). Other researchers have reported that β-sitosterol and Campesterol were the only two phytosterols detectable in blood (1, 5).

The most common phytosterols in tomato oleoresin are β-sitosterol, Campesterol and Stigmasterol as shown below in Table 1, as determined in accordance with the procedure set forth in Example 2 hereof.

TABLE 1

| Levels of Phytosterols in Tomato Oleoresin | |
| --- | --- |
| Total Phytosterols (mg/100 g) | 650-1100 |
| Campesterol (mg/100 g) | 150-220 |
| Stigmasterol, (mg/100 g) | 250-480 |
| β-Sitosterol, (mg/100 g) | 250-400 |

The uncontrolled production of reactive oxygen species (ROS) and arachidonic acid (AA) metabolites contributes to the pathogenesis of cardiovascular disease and cancer. Inflammatory cells infiltrated in the atheroma plaque or tumor, are a major source of ROS and eicosanoids. Therefore, the effects of beta-Sitosterol, a phytosterol from olive oil, on ROS levels such as superoxide anion ($O_2(^-)$), hydrogen peroxide ($H_2O_2$), and nitric oxide (*NO) have been studied (6). AA release and eicosanoid production by phorbol esters (PMA)-stimulated macrophages (RAW 264.7 cells) has also been studied. Beta-sitosterol was shown to decrease the $O_2(^-)$ and ($H_2O_2$) production induced by PMA, and exerted its effects 3-6 hours after preincubation. Beta-sitosterol also reduced the *NO release induced by PMA, which was correlated with the impairment of inducible nitric oxide synthase (iNOS) levels (6).

Prostate cancer and benign prostatic hyperplasia (BPH) are aging-related conditions that affect prostate gland physiology and impair urinary function in men. As men age, their prostate glands slowly enlarge causing (a) obstructive symptoms exemplified by weak and/or intermittent urinary streams, a sense of residual urine in the bladder after voiding, dribbling or leakage at the end of urination, and/or (b) irritative symptoms as exemplified by urgency of micturation, increased frequency of urination, and uracratia. Obstructive and irritative urinary symptoms are commonly referred to as lower urinary tract symptoms (LUTS). The current treatment of prostate cancer, BPH and LUTS symptoms consist of drug therapy, and in extreme cases requires major surgery. The two primary drug classes used are alpha-blockers and 5-alpha-reductase inhibitors, which should be taken for life in order to obtain persistent efficacy. When surgery is conducted, the results are usually positive, but there are certain risks associated with such surgical operations.

US Patent Publication 2005/0031557 ("the 557 Publication") describes an oral composition containing β-carotene, lutein and lycopene, and includes, as potential added ingredients, phytoene and phytofluene, for use as sun protection. This publication does not indicate a preference for a specific amount of either of phytoene or phytofluene relative to lutein or any of the following list of phytochemicals consisting of alpha-carotene, astaxanthin, alpha-cryptoxanthin, beta-cryptoxanthin, zeaxanthin, phytoene, phtyofluene, gamma-carotene and neurosporin. The '557 Publication does not provide a reason for including any of the members of that list in the composition.

Epidemiologic and experimental studies suggest that dietary phytosterols may offer protection from most cancers in Western societies, such as colon, breast and prostate cancer. The possible mechanisms by which phytosterols offer this protection may include the effect of phytosterols on membrane structure, the function of the tumor and host tissue, signal transduction pathways that regulate tumor growth and apoptosis (8), and immune function (9) of the host. Also, the cholesterol metabolism by the host, beta-sitosterol supplementation, reduced cholesterol and other lipids in tumor cell membrane (10). In addition, Table 2 below summarizes the results of several in vitro studies or the effects of phytosterols on human cancer cell lines:

TABLE 2

In vitro studies with various cancer cell lines

| Cell line | tissue | phytosterol | concentration (µM) | parameter | Ref. |
|---|---|---|---|---|---|
| HT-29 | human colon cancer | β-sitosterol | 16 | growth inhibition | (10) |
| LNCaP | human prostate cancer | β-sitosterol | 16 | growth inhibition; reduced PSA levels | (11) |
| MDA-MB-231 | human breast cancer | β-sitosterol | 16 | growth inhibition | (12) |
| | | Campesterol | 16 | growth = unchanged | |
| | | cholesterol | 16 | growth = unchanged | |
| MCF-7 | human breast cancer | SIT | 0.001 to 150 | growth increase | (13) |

Additional studies have been performed in order to identify possible mechanisms by which two common phytochemicals, resveratrol and beta-sitosterol, inhibit the growth of human prostate cancer (14). In these studies, human prostate cancer cells (PC-3 cells) were supplemented with 50 µM resveratrol or 16 µM beta-sitosterol, alone or in combination, for up to 5 days (14). The combination of the two compounds resulted in greater inhibition of growth than either compound alone. Based on these data, it was concluded that these phytochemicals may induce the inhibition of tumor growth by stimulating apoptosis and arresting cells at different locations in the cell cycle, and that the mechanism may involve alterations in the production of ROS and prostaglandin (14).

Additional reports also indicate that a combination of phytosterols and omega-3 fatty acids (n-3) further reduces cardiovascular risk factors (15).

Plant sterols and stanols are reported as lowering the plasma concentrations of hydrocarbon carotenoids, but not those of the oxygenated carotenoids and tocopherols (3, 16). In one report, the ability of plant sterol esters (PSE) in salad dressing to modify plasma lipids and carotenoids was determined in 26 men and 27 women who were fed controlled, weight maintaining, isocaloric diets (17). Consumption of 3.6 g of PSE resulted in decreases in LDL cholesterol (9.7%) and triglycerides (7.3%) but no change in EDL cholesterol was observed. Total plasma carotenoids decreased 9.6% with consumption of PSE. Specifically, there were significant decreases in beta-carotene, alpha-carotene, and beta-cryptoxanthin. Plasma carotenoids on all diets remained within normal ranges. In another study, the data indicate that plant free sterols and PSEs reduced the bioavailability of beta-carotene by approximately 50% and that of alpha-tocopherol by approximately 20% (18).

Notwithstanding the above reported studies, there remains the need for pharmaceutical compositions comprising carotenoids, e.g., lycopene, for therapeutic use.

SUMMARY OF TEE INVENTION

In accordance with the present invention, a pharmaceutical composition for oral administration has been discovered comprising a therapeutically effective amount of a synergistic combination of lycopene and at least one phytosterol wherein the ratio of lycopene to the at least one phytosterol in the pharmaceutical composition is a maximum of about 5:1. Preferably, this composition further includes phytoene, phytofluene, beta-carotene and tocopherols. In a preferred embodiment, the ratio of lycopene to at least one phytosterol is between about 0.9:1 and 4.7:1. Preferably, the ratio of lycopene to at least one phytosterol is less than about 4.0:1, more preferably less than about 3.5:1, and most preferably less than about 3:1.

In accordance with one embodiment of the pharmaceutical composition of the present invention, the composition includes lycopene in an amount of between about 2 and 10 wt. % in combination with at least one phytosterol in the amount of 1 to 5 wt. %.

In accordance with another embodiment of the pharmaceutical composition of the present invention, the lycopene is present in tomato oleoresin in an amount of about 6-15 wt. % and the at least one phytosterol is present in an amount of at least about 1 wt. % Preferably, the pharmaceutical composition includes from about 1.0 to 5 wt. %, and preferably from about 1.5 to 3 wt. % of the combination of phytoene and/or phytofluene. Preferably, the pharmaceutical composition comprises a tomato extract (oleoresin). In a preferred embodiment, at least one phytosterol comprises beta-sitosterol, Campesterol, beta-octasterol, Stigmasterol, and mixtures thereof. Preferably, the at least one phytosterol comprises a mixture of these phytosterols.

In accordance with another embodiment of the present invention, a pharmaceutical composition for oral administration has been discovered comprising a therapeutically effective amount of a synergistic combination of lycopene and at least one phytosterol wherein the ratio of lycopene to the at least one phytosterol in the pharmaceutical composition is a maximum of about 5:1, and wherein the combination produces a synergistic inhibition of prostate cell growth. In a preferred embodiment, the ratio of lycopene to at least one phytosterol is between about 0.9:1 and 4.7:1. Preferably, the ratio of lycopene to at least one phytosterol is less than about 4.0:1, more preferably less than about 3.5:1, and most preferably less than about 3:1.

In accordance with one embodiment of the pharmaceutical composition of the present invention, the composition includes lycopene in an amount of between about 2 and 10 wt. % in combination with at least one phytosterol in the amount of 1 to 5 wt. %.

In accordance with another embodiment of the pharmaceutical composition of the present invention, the lycopene is present in tomato oleoresin in an amount of about 6-15 wt. % and the at least one phytosterol is present in an amount of at least about 1 wt. % Preferably, the pharmaceutical composition includes from about 1.0 to 5 wt. %, and preferably from about 1.5 to 3 wt. % of the combination of phytoene and phytofluene. Preferably, the pharmaceutical composition comprises a tomato extract (oleoresin). In a preferred embodiment, at least one phytosterol comprises beta-sitosterol, Campesterol, beta-octasterol, Stigmasterol, and mixtures thereof. Preferably, the at least one phytosterol comprises a mixture of these phytosterols.

In accordance with another embodiment of the present invention, a pharmaceutical composition for oral administration has been discovered comprising a therapeutically effective amount of a tomato oleoresin including lycopene in an amount of from about 6 to 15 wt. %, phytoene and/or phytofluene in an amount of from about 1.0 to 5.0 wt. %, tocopherols in an amount of from about 1.5 to 4.0 wt. %, beta-carotene in an amount of from about 0.2 to 1.0 wt. %, a total fatty acid content in an amount of from about 50 to 90 wt. %, and at least one phytosterol in an amount such that the ratio of the lycopene to the at least one phytosterol is less than about 5:1. In a preferred embodiment, the ratio of the lycopene to the at least one phytosterol produces a synergistic inhibition of prostate cell growth. Preferably, the ratio of the lycopene to the at least one phytosterol is between about 0.9:1 and 4.7:1, more preferably less than about 4:1, more preferably less than about 3:1, and in a preferred embodiment between about 0.05:1 and 2.1:1. In a preferred embodiment, at least one phytosterol comprises beta-sitosterol, Campesterol, beta-octasterol, Stigmasterol, and mixtures thereof.

In accordance with one embodiment of the pharmaceutical composition of the present invention, the concentration of the at least one phytosterol in the pharmaceutical composition is from about 2.0 to 50.0 wt. %.

In accordance with another embodiment of the pharmaceutical composition of the present invention, the composition additionally includes gamma-carotene, delta-carotene, and Vitamin E.

In accordance with another embodiment of the pharmaceutical composition of the present invention, the ratio of lycopene to the at least one phytosterol is between about 0.1:1 and 3:1.

In accordance with the present invention, a method for producing a pharmaceutical composition for oral administration has been discovered comprising preparing a tomato extract comprising an oleoresin including lycopene in an amount of from about 6 to 15 wt. %, phospholipids in an amount of at least about 0.01 wt. %, a mixture of mono- and di-glycerides in an amount of from about 2 to 6 wt. %, and at least one phytosterol in an amount of from about 1 to 1.5 wt. %, wherein the ratio of the lycopene to the at least one phospholipid is about 2:1, and adding a sufficient additional amount of the at least one phytosterol so as to lower the ratio of the lycopene to the at least one phytosterol to less than about 3:1, and preferably between about 0.1 to 3:1, so as to produce a synergistic inhibition of prostate cell growth.

According to another embodiment of the present invention, the lycopene and phytosterol components of the pharmaceutical compositions of the present invention are preferably naturally occurring and are preferably extracted from tomatoes as pulp. The tomato pulp is suitably extracted to produce an oleoresin that can be converted into the compositions of the present invention, such as by the incorporation of additional amounts of the phytosterols thereinto, and can then be processed into beadlets, or dry powder material. In various embodiments, these compositions are suitably encapsulated in soft-gel capsules, or alternatively, in "hardshell" capsules, or optionally, configured into tablets, or if so desired, into sachet packets, and the like.

Therefore, in accordance with one embodiment of the present invention, a tomato oleoresin can now be provided which, as compared to the known tomato oleoresins described in Table 1, now include levels of phytosterols as follows (once again, as determined in accordance with the procedure set forth in Example 2 herein):

TABLE 3

| Levels of Phytosterols in Tomato Oleoresins of the Invention | |
|---|---|
| Total Phytosterols (mg/100 g) | 1600-6300 |
| Campesterol (mg/100 g) | 300-1300 |
| Stigmasterol (mg/100 g) | 500-1700 |
| β-Sitosterol (mg/100 g) | 300-1200 |

According to another embodiment of the present invention, the tomato oleoresins comprising the compositions of the present invention may contain, in addition to lycopene and phytosterols, phytoene, and phytofluene components, as well as one or more of beta-carotene, gamma-carotene, and delta-carotene, a tocopheral and a phospholipid.

BRIEF DESCRIPTION OF THE DRAWINGS

The subject matter of the present invention may be more fully appreciated with reference to the following detailed description, which in turn refers to the drawings, in which.

DETAILED DESCRIPTION

While the specification concludes with the claims particularly pointing out and distinctly claiming the invention, it is believed that the present invention will be better understood from the following description.

Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified. All measurements made are at 25° C. and normal pressure unless otherwise designated. All temperatures are in Degrees Celsius unless specified otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth. All ranges recited herein include the endpoints, including those that recite a range "between" two values.

All references to singular characteristics or limitations of the present invention shall include the corresponding plural characteristic or limitation, and vice versa, unless otherwise specified or clearly implied to the contrary by the context in which the reference is made. Thus, unless otherwise indicated, as used herein, "a" and "an" include the plural, such that, e.g., "a phytosterol" can mean more than one phytosterol.

All combinations of method or process steps as used herein can be performed in any order, unless otherwise specified or clearly implied to the contrary by the context in which the referenced combination is made.

The pharmaceutical compositions and corresponding methods of the present invention can comprise, consist of, or consist essentially of the essential elements and limitations of the invention described herein, as well as any additional or optional ingredients, components, or limitations described herein or otherwise useful therein. As used herein, "comprising" means the elements recited, or their equivalent in structure or function, plus any other element or elements which are not recited. The terms "having" and "including" are also to be construed as open ended unless the context suggests otherwise.

The present invention provides pharmaceutical compositions comprising lycopene from a wide variety of different sources, including synthetic or other natural sources, such as from tomatoes, from fermentation or by algae or fungi, and one or more phytosterols for therapeutic use. As contemplated herein, lycopene and its precursors phytoene and phytofluene may be found within an oleoresin produced from tomato fruits. Suitable tomato fruits are produced by non-genetically or genetically engineered plants, and preferably contain high concentrations of lycopene, and as referred to above, while also including phytosterols. However, the levels of phytosterols in these known compositions are low, and result in lycopene and phytosterol ratios of about 5:1 and higher. Therefore, in order to prepare the compositions of the present invention from these tomato oleoresins, additional phytosterol(s) must be added in order to lower the lycopene to phytosterol ratio. When the compositions of the present invention are then prepared, they are preferably encased in a soft gel capsule and may additionally comprise an edible oil exemplified by soya oil, pumpkin seed oil, grapeseed oil and the like. Additional suitable delivery methods are also contemplated herein, and are familiar to one of skill in the art.

The lycopene and phytosterol components are preferably processed from tomato fruits into extracts. The components may be concentrated by removing water from the tomato pulp, thereby producing thickened pulps that contain higher concentrations of the phytosterols, such as the lycopene, phytoene and phytofluene components, as well as beta-carotene, gamma-carotene, delta-carotene, vitamin E, and phospholipids. The thickened pulps may be further suitably processed into an oleoresin which can then be processed to form an oleoresin-based emulsion. The tomato oleoresin extract may be encapsulated within soft gel capsules comprising soya oil or alternatively, pumpkin seed oil. The tomato extracts may be optionally formulated into beadlets that may be packaged if so desired in sachet packets, or alternatively, dispersed in suitable carriers (oleoresin is a liquid, and cannot be dried), and processed into powders that may be optionally encapsulated or alternatively, tabletted.

A non-limiting examples of a preferred source of lycopene includes an oleoresin product of tomato known as Lyc-O-Mato® in liquid, oil-dispersible form and provided by LycoRed Ltd., Bear Sheba, Israel, pursuant to their process for recovering a lycopene-rich oleoresin from tomato pulp under U.S. Pat. No. 5,837,311, which is incorporated by reference herein.

Thus, a lycopene-rich oleoresin can be prepared from tomato pulp by pretreating the tomatoes themselves in a conventional way, subjecting them to heat treatment, separating the crushed tomatoes into serum and pulp containing at least 2000 ppm, and preferably from 1600 to 4500 ppm, of lycopene, and preferably with a moisture content not higher than 85%, subjecting the pulp to solvent extraction to extract an oleoresin containing lycopene, separating the spent pulp, and separating the lycopene extract from the solvents to obtain an oleoresin containing lycopene and other oil soluble phytochemicals, and to recover the solvents. In this manner, the oleoresin contains from about 6% to 15% of lycopene, from about 1.0 to 5 wt. % of phytoene and/or phytofluene, from about 1.5 to 4 wt. % of tocopherols, from about 0.2 to 1 wt. % beta-carotene, from about 50 to 70 wt. % of total fatty acids, along with at least one phytosterol in an amount from about 1 to 1.5 wt. %, such that the ratio of the lycopenes to the at least one phytosterol is at least about 4:1. The pharmaceutical compositions of the present invention can then be produced from this oleoresin by adding a sufficient additional amount of at least one phytosterol so as to lower the ratio of lycopene to the at least one phytosterol to less than 4:1, and most preferably less than 3:1, so as to produce a synergistic inhibition of prostate cell growth. These compositions can also include at least about 0.01%, and preferably from about 9.0 to 4.5% of phospholipids and at least about 0.01%, and preferably from about 2 to 6% of a mixture of mono- and di-glycerides.

Therefore, in accordance with the known composition, such as the Lyc-O-Mato® product, containing from 6 to 15% lycopene and 0.6 to 1.1% phytosterols, for these compositions the ratio of lycopene to phytosterols ranges from 5.5 to 25.0, as follows:

| Lycopene | 6% | 7% | 8% | 9% | 10% | 11% | 12% | 13% | 14% | 15% |
|---|---|---|---|---|---|---|---|---|---|---|
| Phytosterol | 0.6% | 0.6% | 0.6% | 0.6% | 0.6% | 0.6% | 0.6% | 0.6% | 0.6% | 0.6% |

-continued

| Ratio | 10.0 | 11.7 | 13.3 | 15.0 | 16.7 | 18.3 | 20.0 | 21.7 | 23.3 | 25.0 |
|---|---|---|---|---|---|---|---|---|---|---|
| Phytosterol | 1.1% | 1.1% | 1.1% | 1.1% | 1.1% | 1.1% | 1.1% | 1.1% | 1.1% | 1.1% |
| Ratio | | 5.5 | 6.4 | 7.3 | 8.2 | 9.1 | 10.0 | 10.9 | 11.8 | 12.7 | 13.6 |

On the other hand, with added phytosterols in accordance with the present invention to these same compositions, thus containing 6 to 15% lycopene with from 1.6 to 6.5% phytosterols, the ratio of lycopene to phytosterols will now range form 0.9 to about 4.7 or less than about 5.0, as follows:

| Lycopene | 6% | 7% | 8% | 9% | 10% | 11% | 12% | 13% | 14% | 15% |
|---|---|---|---|---|---|---|---|---|---|---|
| Phytosterol | 3% | 3% | 3% | 3% | 3% | 3% | 3% | 3.2% | 3.2% | 3.2% |
| Ratio | 2.0 | 2.33 | 2.67 | 3.0 | 3.33 | 3.67 | 4.0 | 4.06 | 4.37 | 4.7 |
| Phytosterol | 6.5% | 6.5% | 6.5% | 6.5% | 6.5% | 6.5% | 6.5% | 6.5% | 6.5% | 6.5% |
| Ratio | 0.92 | 1.08 | 1.23 | 1.38 | 1.54 | 1.69 | 1.85 | 2.0 | 2.15 | 2.31 |

Yet another method for preparing the pharmaceutical compositions of the present invention employs a phytosterol-containing oil and adding a source of lycopene to that phytosterol composition. Phytosterols can thus be in the form of oily compositions containing about 95% phytosterols. Among the phytosterols of a typical phytosterol oil is thus included up to about 10% brassicasterol, from 15 to 30% Campesterol, from 15 to 30% Stigmasterol, and at least about 40% beta-sitosterol. To this phytosterol oil composition can be added lycopene or a source of lycopene. The lycopene source can be provided by the tomato oleoresins discussed above, or by pure lycopene obtained from fermentation, or lycopene from synthetic sources. In any event, sufficient lycopene should be added to the phytosterol oil so that the overall composition preferably includes from about 5 to 10% lycopene. Thus, the remaining 90 to 95% of the composition comprises the phytosterol oil including the specific phytosterols generally in the amounts discussed above. In the overall composition in this regard, the ratio of lycopene to phytosterol will be generally much lower than discussed above, such as from about 0.05:1 to about 0.1:1.

Similarly, pharmaceutical compositions for oral administration comprising a therapeutically effective amount of a synergistic combination of lycopene and at least one phytosterol as described herein, as well as pharmaceutical compositions for oral administration comprising a therapeutically effective amount of a tomato extract comprising an oleoresin including lycopene in an amount of from about 6 to 15 wt. %, phospholipids in an amount of at least about 0.01 wt. %, a mixture of mono- and di-glycerides in an amount of from about 2 to 6 wt. %, and at least one phytosterol in an amount such that the ratio of the lycopene to the at least one phytosterol is less than about 5:1, preferably less than about 4:1, and more preferably less than about 3.5:1, such as less than about 3:1, and wherein the ratio of the lycopene to the at least on phytosterol produces a synergistic inhibition of prostate cell growth as particularly contemplated herein may be prepared by conventional methods familiar to one of skill in the art.

The synergistic pharmaceutical compositions of the present invention, including the exemplified formulas and ratios described herein, can therefore be prepared by any of a variety of known or otherwise effective formulation or manufacturing methods by one of skill in the art.

These methods most typically involve the initial obtaining of a tomato extract or oleoresin of the above Lyc-O-Mato®, subsequent addition of a source of the required added phytosterols, followed by dilution by way of edible oils with a resulting desired concentration of lycopene, phytoene, phytofluene, lutein and phytosterols. Further, as used herein, "consisting essentially of" means that the composition of the present invention contains other components than those specifically identified but are of negligible or neutral effect with respect to the objects of the invention. Thus, it is well known that the tomato extract of Lyc-O-Mato® may contain many components other than those specifically identified in the compositions of the present invention, but said tomato extract contains essentially no other components, or particular ratio of components, affecting the objects of this invention. It is also contemplated herein that various other solutions, mixtures, or other materials may be added to the resulting desired diluted tomato extract before, during, or after further processing. For example, the diluted tomato extract can, in addition to being made into soft gel capsules, then be further diluted, heat-treated, and packaged to form a ready-to-eat or concentrated liquid, or it can be heat-treated and subsequently processed and packaged as a reconstitutable powder, e.g., spray dried with a suitable carrier, dry mixed, or agglomerated.

As contemplated herein, phytosterols for use in the present invention include one or more phytosterols selected from the group consisting of β-Sitosterol, Campesterol, β-Octasterol, and Stigmasterol, and mixtures thereof.

Phospholipids for use with the pharmaceutical compositions disclosed herein, e.g., in an amount of at least about 0.01 wt. % include, for example, phosphatidylcholine, phosphatidylethanolamine, phosphatidylserine, phosphatidylinositol, ceramide-phosphorylcholine (sphingomyelin), ceramide phosphorylethanolamine, and ceramide phosphorylglycerol.

As used herein, a "mixture of mono- and di-glycerides" for use with the compositions disclosed herein, include, for example, 1-palmitoyl-2-oleoyl-glycerol, 1-steryl-1-oleoyl-glycerol, and 1-palmitoyl-2-stearyl-glycerol.

Although the present invention has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

EXAMPLES

Example 1

The Combined Anticancer Effect of Phytosterols and Lycopene

The goal of this study was to determine the effects of various phytosterols alone and in combination with low concentrations of lycopene on the proliferation of human prostate cancer cells.

Methods:

Cell culture and cell proliferation assay: LNCaP, human androgen dependent prostate cancer cells, were purchased from American Type Culture Collection (Rockwell, Md.). Cells were grown in RPMI1640 containing 0.6 µg/ml insulin. All culture media were supplemented with L-glutamine (2 mM), penicillin (100 U/ml), streptomycin (0.1 mg/ml), nystatin (12.5 µg/ml), and 10% FCS. Cells were seeded in medium containing 3% FCS or 3% DCC phenol red free medium and 10 mM HEPES onto 96- and 6-multiwell plates ($4-7\times10^3$ and $1.7\times10^5$ cells/well, respectively). One day later, the medium was changed to 0.5% FCS or 0% medium for an additional one day of incubation. Then the medium was changed to one containing the micronutrients (phytosterols, carotenoids, phospholipids, etc.) at the indicated concentrations and incubation was continued for 1-3 days. In order to assure that the agent was continuously present during prolonged incubation, the medium was replaced daily with one containing fresh carotenoids. Lycopene was dissolved in tetrahydrofuran at a concentration of 2 mM and stored at $-20°$ C. Immediately before the experiment, the stock solution was added to the cell culture medium. The final concentration of lycopene in the medium was measured by spectrophotometry after extraction in 2-propanol and n-hexane:dichloromethane [3H]thymidine incorporation assay was performed in 96-multiwell plates. Cells were incubated with 1.25-2.50 uCi/well of [3H]thymidine (specific radioactivity 5 mCi/mmol in µCi/well) for one to four hours. The nucleotide incorporation was stopped by addition of unlabeled thymidine (0.5 µmol). The cells were then trypsinized and collected on a glass-fiber filter using a cell harvester (Inotech). Radioactivity was determined by a radioactive image analyzer (BAS 1000, Fuji).

All procedures were performed under dim light in order to prevent carotenoid degradation.

Results:

LNCaP prostate cancer cells were incubated in the presence of a physiological concentration (0-50 µM) of phytosterols as provided in FIG. 1. When tested alone, β-sitosterol inhibited prostate cancer cell proliferation in a dose dependent manner (open circles, FIG. 1A) whereas the other tested phytosterols, Campesterol, β-octasterol and Stigmasterol (open circles, FIGS. 1B-1D, respectively) did not have any effect on cell growth inhibition at the tested concentration. However, in combination with a 0.4 µM concentration of lycopene (which alone did not inhibit proliferation in vitro (as seen from FIG. 1E)) all four of the tested phytosterols exhibited a substantial synergistic inhibition of prostate cell growth in vitro.

Figure 1A:
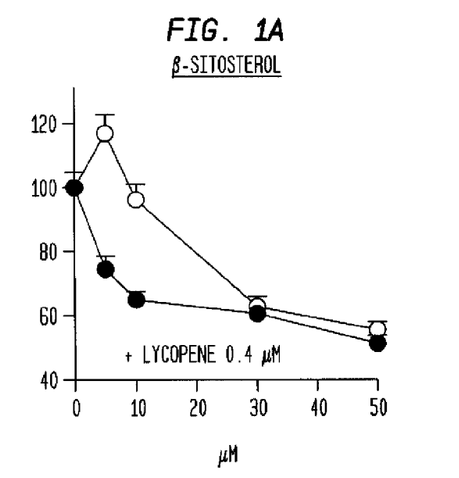
FIG. 1A is a graphical representation of cell growth inhibition based on percent of the control of LNCaP cells resulting from treatment with β-Sitosterol and the combination of β-Sitosterol with 0.4 µM lycopene.
Figure 1B:
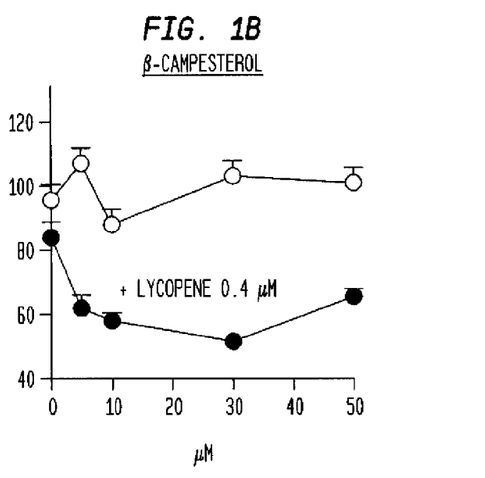
FIG. 1B is a graphical representation of cell growth inhibition resulting from percent of the control of LNCaP cells based on treatment with β-Campesterol and the combination of β-Campesterol with 0.4 µM lycopene.
Figure 1C:
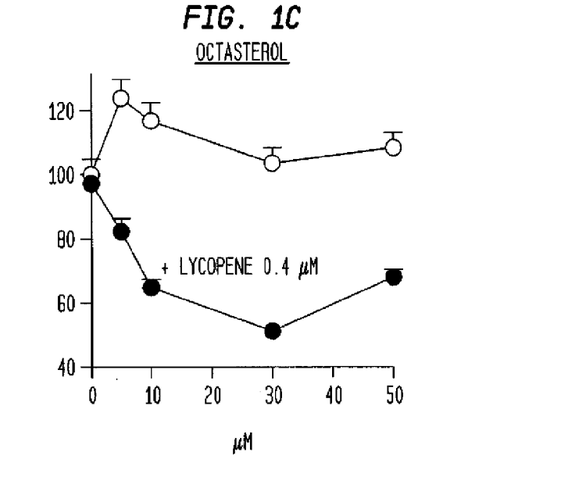
FIG. 1C is a graphical representation of cell growth inhibition resulting from percent of the control of LNCaP cells based on treatment with β-Octosterol and the combination of β-Octosterol 0.4 µM with lycopene.
Figure 1D:
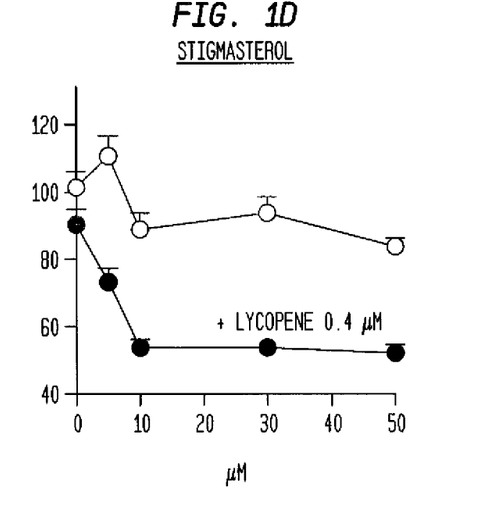
FIG. 1D is a graphical representation of cell growth inhibition resulting from percent of the control of LNCaP cells based on treatment with β-Stigmasterol and the combination of β-Stigmasterol with 0.4 µM lycopene.
Figure 1E:
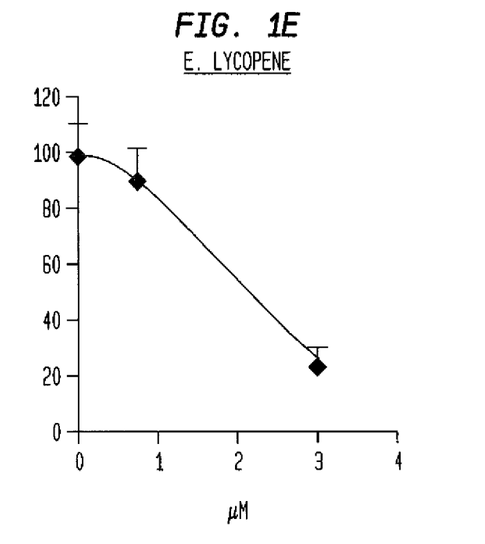
FIG. 1E is a graphical representation of cell growth inhibition based on percent of the control of the LNCaP cells resulting from treatment with lycopene at several concentrations.
Figure 2:
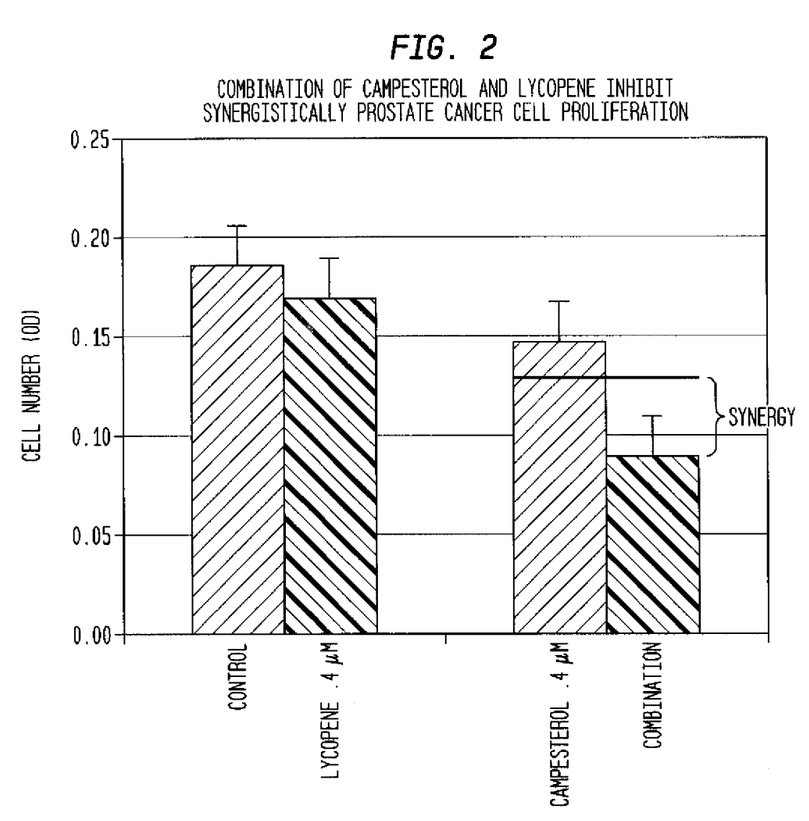
FIG. 2 is a graphical representation of the synergistic inhibition of human androgen-dependent prostate cancer cell proliferation in vitro in the presence of a combination of lycopene and the phytosterol Campesterol. In these experiments, LNCaP cells were preincubated for 24 hours in 0.5% serum and then growth (quantified by measuring thymidine incorporation) was stimulated by 1 nM DHT. Stimulated cells were treated for 3 days with the indicated concentration of the phytosterols alone, or in combination with 0.4 µM lycopene. Data presented are the mean±SE of 2-3 independent experiments performed in quadruplicates.

Furthermore, referring to FIG. 1E when lycopene was tested alone the result shown therein where obtained.

FIGS. 1A-1E. LNCaP cell were preincubated for 24 hours in 0.5% serum and then growth (thymidine incorporation) was stimulated by 1 nM DHT. Stimulated cells were treated for 3 days with the indicated concentrations of the phytosterols alone, or in combination with 0.4 µM Lycopene. Data presented are the mean±SE of 2-3 independent experiments performed in quadruplicates.

Example 2

The specific method for calculation of the total phytosterols content in a given sample such as the Lyco-O-Mato oleoresin was carried out as follows:

The Lyco-O-Mato sample was saponified by weighing about to 2 grams of the oleoresin or 10 grams of lycopene crystals (0.0001 g) into a 250 ml Erlenmeyer flask. 100 ml of 0.8 M KOH in ethanol was added, and with stirring heated at 80° C. under reflux for 1 hour. 100 ml of distilled water was added, and the mixture was transferred into a 500 ml separating funnel. 100 ml of hexane was added, vigorously shaken, and allowed to stand for phase separation and collection of the hexane layer. This extraction was repeated three times with 50 ml hexane each time. All hexane extracts were collected and washed with distilled water at a pH of 7. The hexane extract was dried over anhydrous magnesium sulfate and completely evaporated using a rotary evaporator. The material obtained after saponification was weighed.

The saponified material was then dissolved in n-hexane (HPLC grade) and transferred to a 50 ml volumetric flask and diluted with n-hexane to volume. The above solution was diluted with ethanol (HPLC grade) to obtain a solution of about 0.8 mg/ml of saponified sample. The required dilution was calculated as follows: $Dil_{ssa}=W_{ssa}/0.8/50$. The ethanol solution was filtered through 0.45 µm PTFE filter into an amber autosampler vial and injected into the HPLC column. The HPLC system utilized was based upon the reverse phase separation technique, and was equipped with an autosampler, variable wavelength or diode array detector data system.

A working standard solution was prepared by weighing about 50 mg of Stigmasterol standard into a 50 ml volumetric flask. 20 ml of n-hexane (HPLC grade) was added and sonicated a water bath at room temperature for 1 to 2 minutes. The flask was filed to volume with n-hexane. 50 ml of this solution was diluted to 25 ml with ethanol (HPLC grade). The working standard solution was filtered with PTFE 0.45 µm filter into an amber autosampler vial and injected into HPLC. In this system the relative retention times of a Campesterol peak was not less than 1.03, of β-Sitosterol not less than 1.09, and Stigmasterol 1.00. The RSD of peak area in the working standard solution should not be greater than 2%.

The total phytosterols content was calculated as follows:

$$\text{Total Phytosterols, \%} = \frac{A_{SA} \times P \times D_{SA} \times W_{st} \times 100}{A_{ST} \times c \times w_{SA}}$$

$A_{SA}$=Sum of phytosterols peak area in sample
$A_{ST}$=Stigmasterol peak area of standard
$W_{st}$=Weight of Stigmasterol standard, mg
$W_{SA}$=Weight of sample, mg
P=Potency of standard/100 (905%/100=0.95)
$D_{SA}$=Dilution factor of sample ($50\times Lil_{ssa}-50\times W_{ssa}/0.8/50-W_{ssa}/0.8$
$W_{ssa}$=SEE SECTION 8.2.2
$D_{ST}$=Dilution factor of standard
$D_{SA}$ Dilution factor of sample
$D_{SA}$=Dilution factor of standard Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

REFERENCES

1. Weststrate, J. A. and Meijer, G. W. Plant sterol-enriched margarines and reduction of plasma total- and LDL-cholesterol concentrations in normocholesterolaemic and mildly hypercholesterolaemic subjects, Eur J Clin Nutr. 52: 334-43, 1998.
2. Jones, P. J. and Raeini-Sarjaz, M. Plant sterols and their derivatives: the current spread of results, Nutr Rev. 59: 21-4, 2001.
3. Ling, W. H. and Jones, P. J. Dietary phytosterols: a review of metabolism, benefits and side effects, Life Sci. 57: 195-206, 1995.
4. Moghadasian, M. H. Pharmacological properties of plant sterols in vivo and in vitro observations, Life Sci. 67: 605-15, 2000.
5. Awad, A. B., Garcia, M. D., and Fink, C. S. Effect of dietary phytosterols on rat tissue lipids, Nutr Cancer. 29: 212-6, 1997.
6. Moreno, J. J. Effect of olive oil minor components on oxidative stress and arachidonic acid mobilization and metabolism by macrophages RAW 264.7, Free Radic Biol Med. 35: 1073-81, 2003.
7. Hui-lian, W., Qian-rong, L., jian, Y., Zhao-feng, L., and Yu-zhen, W. The protective effect and mechanism of soybean oil and its extracts on DNA damage in human ECV304 cells exposed to UV-C, Biochim Biophys Acta. 1626: 19-24, 2003.
8. Choi, Y. H., Kong, K. R., Kim, Y. A., Jung, K. O., Kil, J. H., Rhee, S. H., and Park, K. Y. Induction of Bax and activation of caspases during beta-sitosterol-mediated apoptosis in human colon cancer cells, Int J. Oncol. 23: 1657-62, 2003.
9. Bouic, P. J. The role of phytosterols and phytosterolins in immune modulation: a review of the past 10 years, Curr Opin Clin Nutr Metab Care. 4: 471-5, 2001.
10. Awad, A. B., Chen, Y. C., Fink, C. S., and Hennessey, T. beta-Sitosterol inhibits HT-29 human colon cancer cell growth and alters membrane lipids, Anticancer Res. 16: 2797-804, 1996.
11. von Holtz, R. L., Fink, C. S., and Awad, A. B. beta-Sitosterol activates the sphingomyelin cycle and induces apoptosis in LNCaP human prostate cancer cells, Nutr Cancer. 32: 8-12, 1998.
12. Awad, A. B., Downie, A. C., and Fink, C. S. Inhibition of growth and stimulation of apoptosis by beta-sitosterol treatment of MDA-MB-231 human breast cancer cells in culture, Int J Mol. Med. 5: 541-5, 2000.
13. Ju, Y. H., Clausen, L. M., Allred, K. F., Almada, A. L., and Helferich, W. G. beta-Sitosterol, beta-Sitosterol Glucoside, and a Mixture of beta-Sitosterol and beta-Sitosterol Glucoside Modulate the Growth of Estrogen-Responsive Breast Cancer Cells In Vitro and in Ovariectomized Athymic Mice, J. Nutr. 134: 1145-51, 2004.
14. Awad, A. B., Burr, A. T., and Fink, C. S. Effect of resveratrol and beta-sitosterol in combination on reactive oxygen species and prostaglandin release by PC-3 cells, Prostaglandins Leukot Essent Fatty Acids. 72: 219-26, 2005.
15. Normen, L., Shaw, C. A., Fink, C. S., and Awad, A. B. Combination of phytosterols and omega-3 fatty acids: a potential strategy to promote cardiovascular health, Curr Med Chem Cardiovasc Hematol Agents. 2: 1-12, 2004.
16. de Jong, A., Plat, J., and Mensink, R. P. Metabolic effects of plant sterols and stanols (Review), J Nutr Biochem. 14: 362-9, 2003.
17. Judd, J. T., Baer, D. J., Chen, S. C., Clevidence, B. A., Muesing, R. A., Kramer, M., and Meijer, G. W. Plant sterol esters lower plasma lipids and most carotenoids in mildly hypercholesterolemic adults, Lipids. 37: 33-42, 2002.
18. Richelle, M., Enslen, M., Eager, C., et al. Both free and esterified plant sterols reduce cholesterol absorption and the bioavailability of beta-carotene and alpha-tocopherol in normocholesterolemic humans, Am J Clin Nutr. 80: 171-7, 2004.
19. Valsta et al., British Journal of Nutrition (2004), 92, 671-678

The invention claimed is:

1. A pharmaceutical composition for oral administration of a tomato oleoresin consisting essentially of 2-15 wt. % of lycopene, phytoene, phytofluene, tocopherol, beta-carotene, and fatty acids, wherein said tomato oleoresin has a lycopene to phytosterols ratio of from 0.9:1 to 4.7:1 and wherein said phytosterols are 300-1200 mg/100 g of tomato oleoresin of beta-sitosterol, 300-1300 mg/100 g of tomato oleoresin of campesterol and 300-1200 mg/100 g of tomato oleoresin of stigmasterol.

2. The pharmaceutical composition of claim 1 wherein said ratio of said lycopene to said phytosterols is between about 0.05:1 and 0.1:1.

3. The pharmaceutical composition of claim 1, wherein said lycopene is present in an amount of between about 2 and 10 wt. % and said phytosterols are in an amount of from about 1 to 5 wt. %.

4. The pharmaceutical composition of claim 1 wherein said lycopene is present in an amount of about 6 wt. % and said phytosterols are present in an amount of at least about 3 wt. %.

5. The pharmaceutical composition of claim 1 wherein said phytoene and said phytofluene are present in an amount from about 1.0 to 5 wt. %.

* * * * *